United States Patent
Scussel et al.

(10) Patent No.: US 12,136,424 B2
(45) Date of Patent: Nov. 5, 2024

(54) DIVER'S VOICE COMMUNICATION SYSTEM

(71) Applicant: Teledyne Instruments, Inc., Thousand Oaks, CA (US)

(72) Inventors: Ken Scussel, East Falmouth, MA (US); Thomas W. Altshuler, Erie, CO (US); Andrey K. Morozov, North Falmouth, MA (US); Michael J. Coryer, West Wareham, MA (US)

(73) Assignee: TELEDYNE INSTRUMENTS, INC., Thousand Oaks, CA (US)

( * ) Notice: Subject to any disclaimer, the term of this patent is extended or adjusted under 35 U.S.C. 154(b) by 0 days.

(21) Appl. No.: 18/094,056

(22) Filed: Jan. 6, 2023

(65) Prior Publication Data
US 2024/0233730 A1    Jul. 11, 2024

Related U.S. Application Data

(60) Provisional application No. 63/299,307, filed on Jan. 13, 2022.

(51) Int. Cl.
| | |
|---|---|
| *G10L 15/22* | (2006.01) |
| *A61B 5/00* | (2006.01) |
| *G08C 23/02* | (2006.01) |
| *G10L 13/00* | (2006.01) |
| *G10L 15/26* | (2006.01) |
| *H04B 11/00* | (2006.01) |

(Continued)

(52) U.S. Cl.
CPC ............ *G10L 15/26* (2013.01); *A61B 5/0002* (2013.01); *G08C 23/02* (2013.01); *G10L 13/00* (2013.01); *H04B 11/00* (2013.01); *H04B 13/02* (2013.01); *H04Q 9/00* (2013.01)

(58) Field of Classification Search
CPC ...................................................... G10L 15/22
See application file for complete search history.

(56) References Cited

U.S. PATENT DOCUMENTS

| | | |
|---|---|---|
| 7,187,623 B2 | 3/2007 | Green et al. |
| 7,362,653 B2 | 4/2008 | Green et al. |
| 9,383,428 B2 | 7/2016 | Green et al. |

(Continued)

OTHER PUBLICATIONS

Wu, Hao, Qingzeng Song, and Guanghao Jin. "Deep learning based framework for underwater acoustic signal recognition and classification." Proceedings of the 2018 2nd International Conference on Computer Science and Artificial Intelligence. 2018. (Year: 2018).*

(Continued)

*Primary Examiner* — Jialong He
(74) *Attorney, Agent, or Firm* — McAfee & Taft

(57) ABSTRACT

Disclosed is a diver's voice communication system which utilizes AI speech recognition, speech-to-text conversion with the ability to adapt to diver speech distortion resulting from hyperbaric helium-oxygen conditions and text transmission using underwater acoustic digital communication. Additionally, the communication system provides the ability to use speech commands in a digital form to control underwater autonomous devices. Further, the digital communication system provides the ability to track and communicate with a large number of divers or with select divers from a large group.

8 Claims, 6 Drawing Sheets

(51) Int. Cl.
*H04B 13/02* (2006.01)
*H04Q 9/00* (2006.01)

(56) References Cited

U.S. PATENT DOCUMENTS

2004/0196180 A1* 10/2004 Hollis .................... G06F 1/163
                                                          367/134
2014/0051352 A1*  2/2014 Wolfe .................... H04B 13/02
                                                          455/40
2015/0304054 A1* 10/2015 Imran .................... H04R 1/44
                                                          367/132

OTHER PUBLICATIONS

S&I Organization CMRE; Janus, The CMRE Underwater Communication Protocol Becomes NATO Standard; Science and Technology Organization Centre for Maritime Research and Experimentation; Press Release; p. 1 2017.
Nordrum, Amy; NATO Unveils Janus, First Standardized Acoustic Protocol for Undersea Systems—The New Acoustic Communications Protocol is a Step Toward an Internet of Underwater Things; IEEE Spectrum; pp. 1-7 Jul. 11, 2017.
Woodward, B.; Underwater Telephony: Past, Present and Future; Colloque Dei Physique C2; pp. 591-594 1990.
Woodward, B. et al.; Digital Underwater Acoustic Voice Communications; IEEE Journal of Oceanic Engineering, vol. 21, No. 2; pp. 181-192 Apr. 1996.
U.S. Navy Diving Manual 2016, Chapter 7, Scuba Air Diving Operations, Section 7-8.5; Diver Communications; pp. 7-40 2016.

* cited by examiner

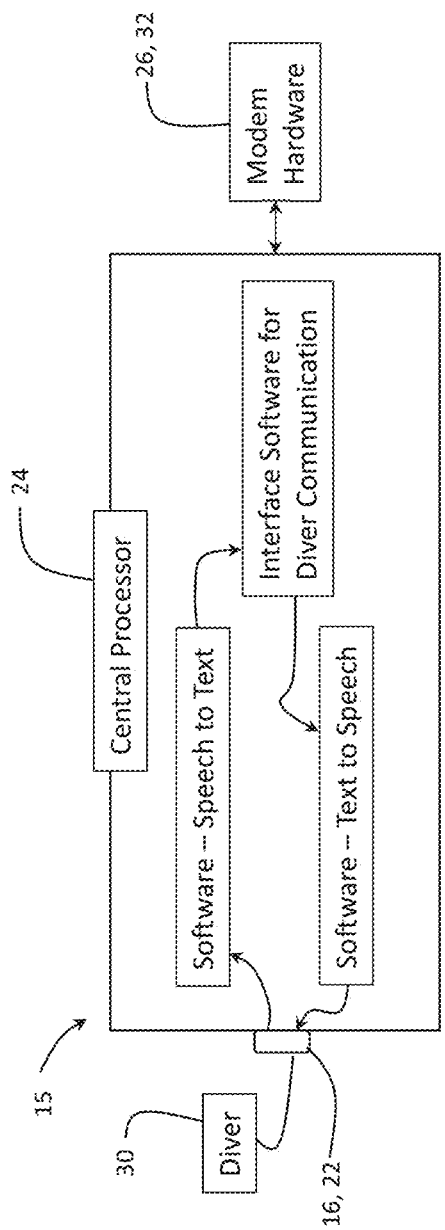

DIVER'S VOICE COMMUNICATION SYSTEM

CROSS REFERENCE TO RELATED APPLICATIONS

The present application claims priority to U.S. Provisional Application No. 63/299,307 filed on Jan. 13, 2022 which is incorporated herein.

BACKGROUND

Self-contained underwater breathing apparatus, commonly referred to as SCUBA, allows individuals to operate underwater for extended periods of time. Advances in gas mixtures have also extended the operational periods and depths of operations. For simple recreational dives, divers typically rely upon hand signs, banging a metal tool on the gas tank or slate boards for underwater communications. However, dive teams performing underwater construction or military operations need real-time, two-way communication between divers and between divers and surface personnel.

Currently available analog systems lack the ability to work with a plurality of dive groups, to address message to different divers, to track divers and do not provide secure or reliable communications. Additionally, current systems lack the ability to compensate for speech distortion in hyperbaric helium-oxygen diving gas conditions. Further, the divers lack the ability to use control panels, keyboards or other similar devices suitable for sending commands to autonomous underwater vehicles (AUV) or other devices. Still further, current systems do not provide for continuous health monitoring of a diver, e.g. transmission of digital biometric and sensory data, images.

SUMMARY

To provide for the needs of the industry, this disclosure describes a Diver Voice Communication System (DVCS). The DVCS includes a first digital voice transmitter-receiver sub-system. The sub-system include a diver mask with headphones and microphone, a microcomputer programmed with speech to text software and text to verbal message software, and an underwater digital acoustic telemetry modem. A diver's voice communication system based on speech recognition, speech-to-text conversion, and text transmission using acoustic digital communication. The system makes the best use of the limited acoustic bandwidth and compares favorably from known prototype and analogues by the following qualities. The processor of the diver system including the training program with artificial intelligent program, which will adapt to the specific voice conditions of the diver using high pressure breathing gas mixture and after training the advanced voice communication system will have ability to compensate voice distortions in a high-pressure diver equipment with special breathing gas mixture. The voice commands transformed in a text-digital form are can also be used for an underwater robotics control. The digital communication system can track the location of communicating divers, by utilizing timing from synchronization system. This voice communication can be broadcast to multiple users, or it can be addressed to one of them. It can work with one or many diver clusters with the identification of each diver and its cluster. In addition, the same system will be able to transmit images, along with other telemetry such as diver biometrics and sensor data on diver equipment. The disclosed system will provide an advanced digital network suitable for carrying out two-way communication between submerged divers as well as between personnel at the surface and submerged divers.

BRIEF DESCRIPTION OF THE DRAWINGS

FIGS. 1 & 6 provide schematic views of a diver's voice communication system used by a diver.

FIG. 7 provides an example look up table used for selective communication between divers or between a diver and an autonomous vehicle.

DETAILED DESCRIPTION

Figure 1:
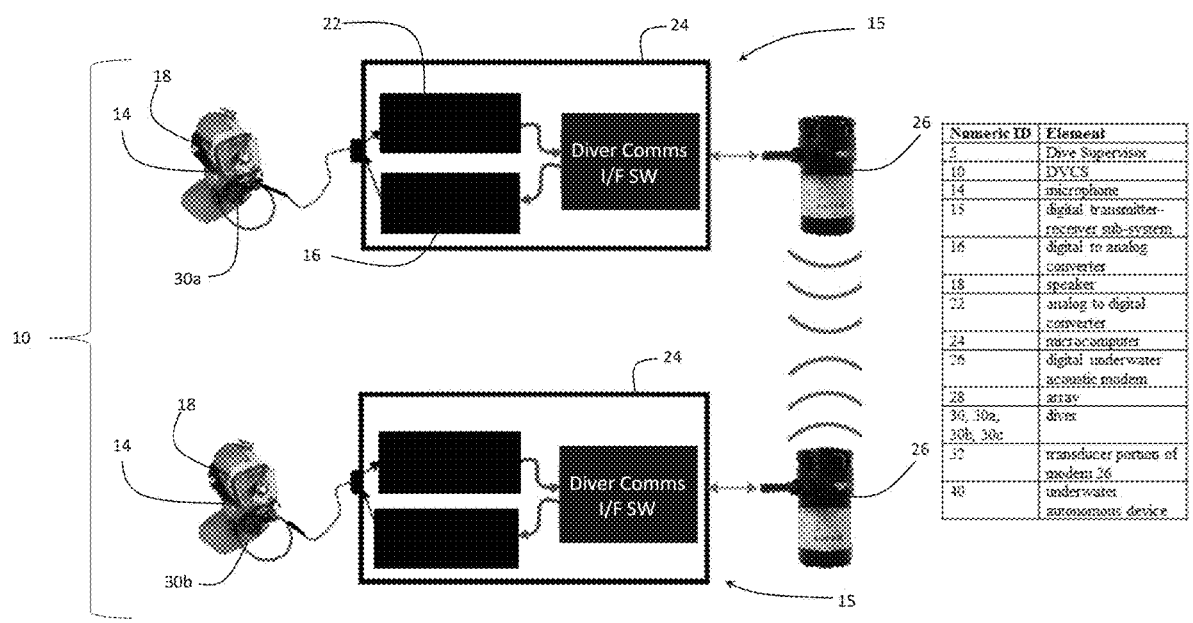

This disclosure provides a diver's voice communication system 10 (DVCS) based on speech recognition, speech-to-text conversion and text transmission using underwater acoustic digital communication. DVCS 10 includes multiple digital transmitter-receiver sub-systems 15. With reference to FIGS. 1 and 6, the digital transmitter-receiver sub-system 15 includes a microphone 14, a digital-to-analog converter 16 with an amplifier and earphones or a speaker 18, an analog-to-digital converter 22, a microcomputer, a microprocessor or other suitable programmable device 24, and a digital underwater acoustic modem 26. Each modem 26 includes a transducer 32 or other suitable component for transmitting the signal. For the purposes of the remainder of this disclosure, the programmable device incorporated into each communication unit will be referred to as microcomputer 24. Use of multiple sub-systems 15 by multiple divers will allow for communication between divers. Use by a corresponding supervisor sub-system will allow for communication between a diver supervisor and the divers.

Figure 2:
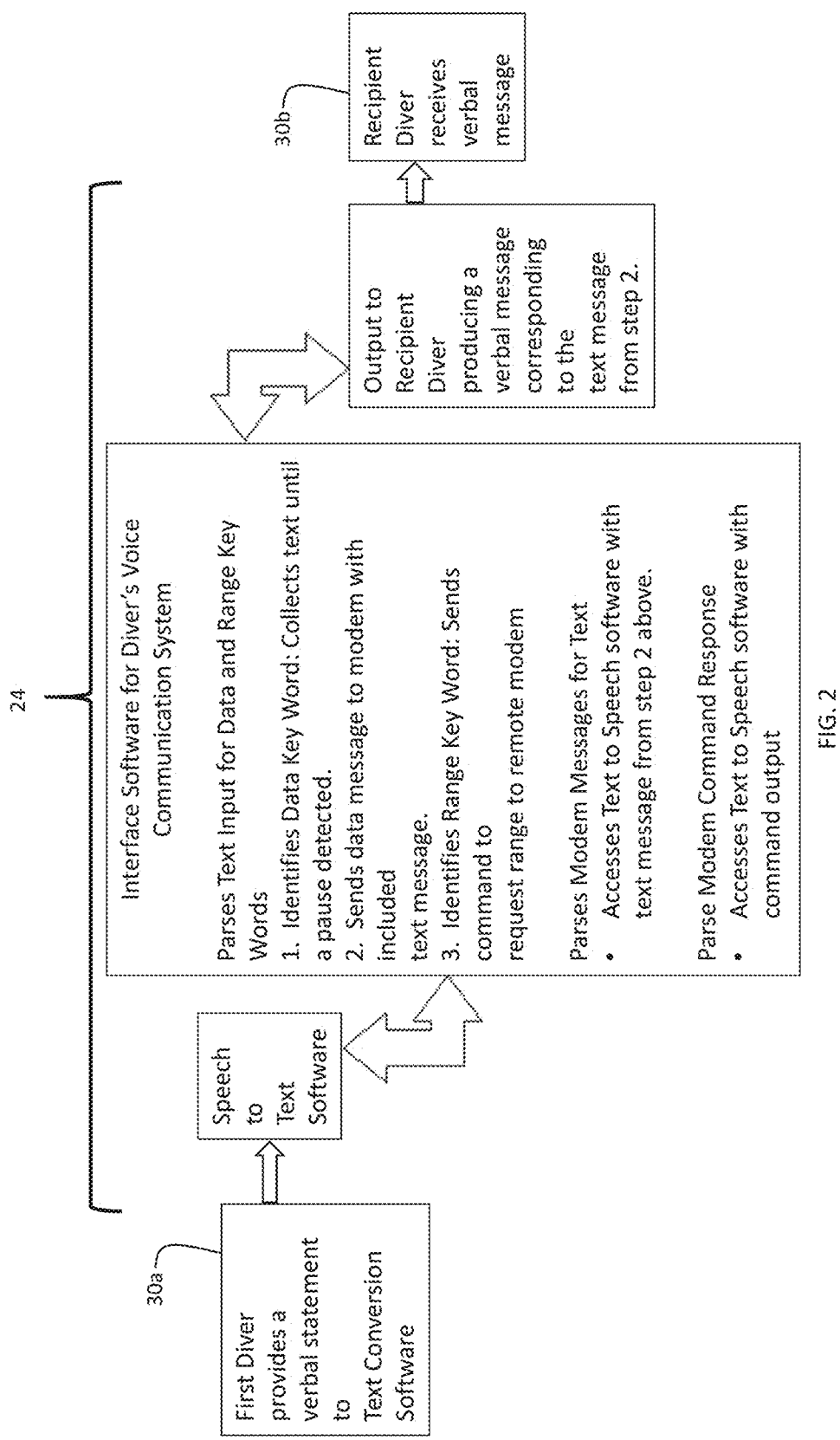
FIG. 2 provides a process flow diagram of the operation as managed by a central processor or microcomputer incorporated into the diver's voice communication system.
Figure 3:
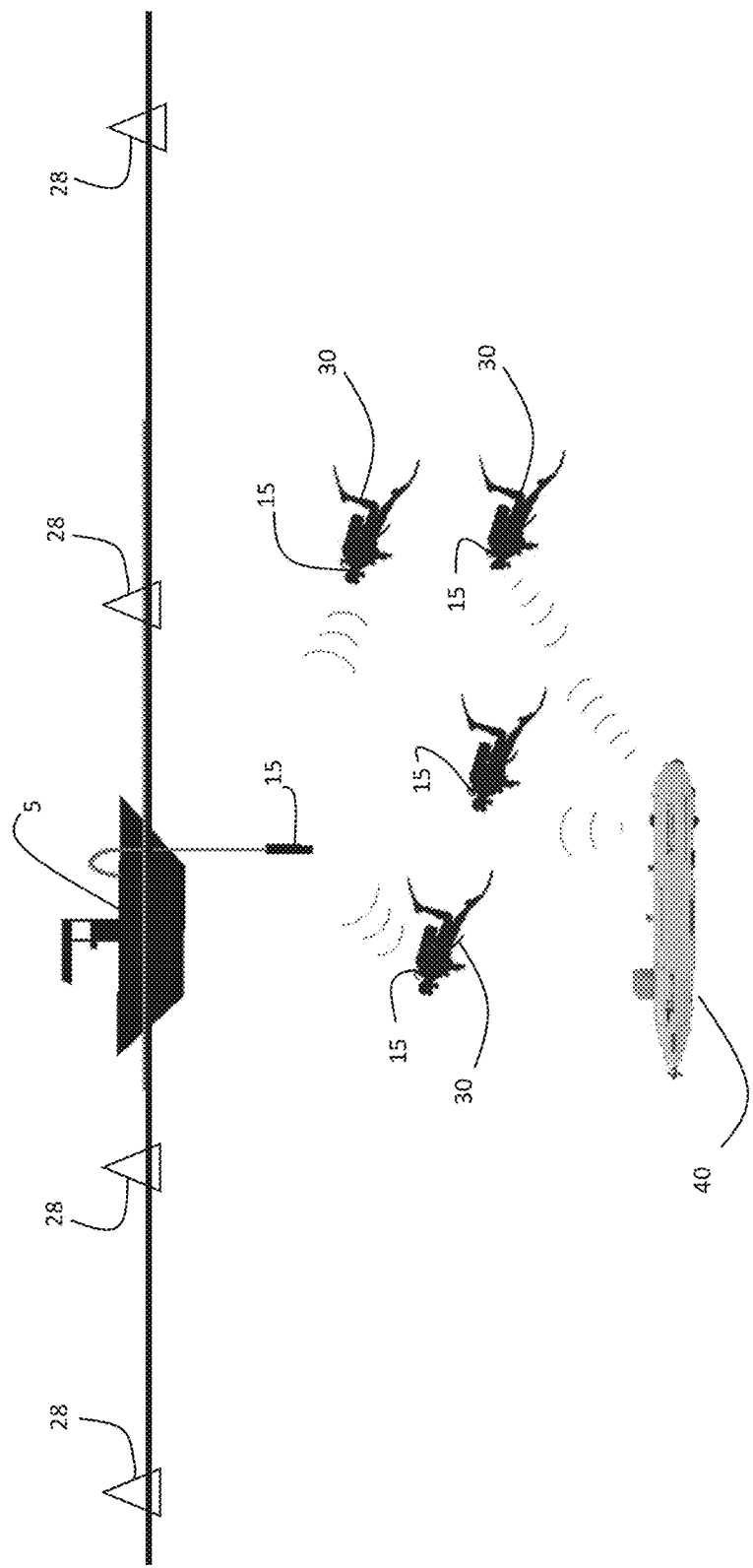
FIG. 3 depicts the diver's voice communication system in use between divers, underwater autonomous devices and a surface dive supervisor aboard a surface vessel.

As reflected in FIGS. 1, 2 and 6, microcomputer 24 includes speech recognition software which incorporates an artificial intelligent (AI) learning system. An example of a suitable speech recognition software is the open source software known as Vosk (https://alphacephei.com/vosk), supplemented with an improved dictionary and adjustment of the acoustic model for underwater conditions. This software package includes artificial intelligence (AI) learning suitable for use in the present invention. In particular, the program provides the ability to adapt to the specifics of diver speech in hyperbaric helium-oxygen conditions in a high-pressure mask. The text to speech application may use for example the open source eSpeak software package. One suitable audio system is the Ocean Technology Systems EM-OTS-2 & EDM-2SM Earphone-Mic assembly.

The voice commands transformed in a text-digital form are also used for control of underwater autonomous devices and vehicles (AUV) 40. The commands to autonomous vehicles would include a vehicle identifier and command. Some example commands are "launch, return, end, surface, and drop". When incorporated as part of an AUV 40, digital transmitter-receiver sub-system 15 may optionally omit the conversion of the text message to an audible voice message. The system makes the best use of the limited acoustic bandwidth and the benefits of digital communications. This provides reliable and secure voice communications with much higher quality than existing analog systems. DVCS 10 may also include a receiving array 28 or several remote receiving points 28 on the sea surface. Receiving array 28 will include programming suitable for receiving signals from GPS satellites appropriate for navigation purposes thereby permitting tracking of divers utilizing DVCS 10. DVCS 10 permits voice communication between multiple users. Alternatively, through selection or use of simple table look-up, communications can be directed to a single select diver 30. The table identifies divers as "Diver/Vehicle Name, Modem Address". The diver simply states for example "message to Max", pause, "we need to return in five minutes." When properly configured, DVCS 10 can provide communication between 250 receiver units, i.e. divers 30 or underwater autonomous devices 40 and, as above referenced, select communication with a single diver's 30 DVCS 10. Thus, DVCS 10 provides for private communication between divers 30 or between a single diver 30 and an autonomous underwater device 40 or between a single diver 30 and a dive supervisor 5 on the surface. In another embodiment, DVCS 10 can identify a select group of receivers, e.g. a cluster of receivers, and direct communication only to the desired cluster. As will be described below, DVCS 10 also provides the ability to transmit audio/video and high-definition images, along with other telemetry such as diver biometrics and sensor data on diver equipment. Thus, DVCS 10 provides an advanced digital network with characteristics not available with existing analog systems.

The microcomputer 24 converts speech into text messages and transmits the message via serial port to the acoustic modem 26. The acoustic modem 26 transmits the data in water using a transducer 32 with the Teledyne acoustic signaling protocol. Digital underwater acoustic modem 26 has the following parameters: frequency band –20-30 kHz, source level: 175 dB re 1µPa@1 m; typical range–2 km, bit rate 2400 bit/s (MFSK)/15360 bits/s (PSK). For the remainder of this disclosure digital underwater acoustic modem 26 will be referred to as modem 26.

DVCS 10 supports secure and reliable data transmission while simultaneously identifying and tracking the digital transmitter-receiver sub-systems 15 of communicating divers 30. A message broadcast from the surface can be received by multiple divers 30 or a single targeted diver 30. The system can work with a single diver 30 or clusters of divers 30 simultaneously. The conversion of speech to text acts as a data compression method as text communication requires less bandwidth over the transmission frequency. Thus, by converting speech to text DVCS 10 maximizes the potential of the limited bandwidth available in the acoustic channel. The digital ultra-compact modem has capabilities of tracking communicating divers. Digital communication is more reliable and secure than its prior-art analog systems prototypes. A diver supervisor on a boat shall have a topside communication interface with a speaker 18 and microphone 14 typically in a headset 5 and a PC or other microprocessor for speech to text conversions and for simultaneous viewing of text communication and range tracking of the divers. In some embodiments, modems 26 include acoustic telemetry capabilities that allow DVCS 10 to determine the distance between each DVCS 10 subsystem within receiving range.

In the same manner as communication occurs between divers 30, digital voice commands can be used to operate an underwater autonomous device 40. Specifically, underwater autonomous device 40 will include DVCS 10 having microcomputer 24 programmed to receive commands from a diver 30 after the command has been converted to a digital signal and interpret such digital commands in a manner to control operation of underwater autonomous device 40. In addition, DVCS 10 will be able to transmit audio/video, high-resolution images, along with other telemetry such as diver biometrics and sensor data on diver equipment. This will provide advanced voice communications with characteristics not available with current analog systems.

The software included in digital transmitter-receiver sub-system 15 will provide the ability to compensate for voice changes resulting from the use of various breathing gas mixtures delivered under pressure to diver 30 and other subsurface conditions. Thus, the software included in digital transmitter-receiver sub-system 15 will compensate for voice distortions resulting from diver equipment and gases used as well as other conditions. As such, the software includes programming which controls a voice recognition system managed by artificial intelligence. The software provides a voice to text conversion via a speech recognition algorithm known as Vosk (https://alphacephei.com/vosk/) to enhance communication over the available bandwidth. Thus, the diver will speak the desired communication and digital transmitter-receiver sub-system 15 will automatically convert the verbal command to a text message, digital transmitter-receiver sub-system 15 will transmit the text message to the target receiver associated with a second digital transmitter-receiver sub-system 15 and the second digital transmitter-receiver sub-system 15 will convert the text message to a voice communication for the recipient diver 30 to hear.

All acoustic messages from Diver 30a to Diver 30b are sent with a signal acquisition section, packet header, and optional packet data. The acquisition section is used by modem 26 to begin receiving and decoding the acoustic message. The fixed size and packet header format contains attributes describing the packet data such as packet type, data size, data modulation, transmitter address (1 byte, values 0-255), and receiver address (1 byte, values 0-255). The packet type indicates the format of the packet data. The data size parameter indicates the number of bytes of data. The modulation indicates the acoustic baud rate. The addresses indicate which modem 26 is sending and which modems 26, i.e. modem address(s), should receive the packet. Modems 26 whose address don't match the receiver address do not decode the packet data. The packet data is of variable size and format based on parameters in the header.

Additionally, DVCS 10, in connection with appropriate sensors secured to diver 30 as well as sensors carried by the diver's equipment, provides the ability to transmit data related to the diver's health and the operational status of the diver's equipment to a third party such as a dive supervisor 5 or unit commander. Medical sensors may include: temperature, blood pressure, heart rate, ECG, EEG, and oxygen saturation (sO2). External operational sensors carried by diver 30 may include: water pressure (depth), water temperature, and relative water clarity. Each sensor will be connected via analog-digital converters to modem 26 of digital transmitter-receiver sub-system 15. Data from the various sensors will be transmitted in parallel with the voice to text communication thereby allowing the dive supervisor 5 to monitor the health and working conditions of each diver 30.

Figure 4:
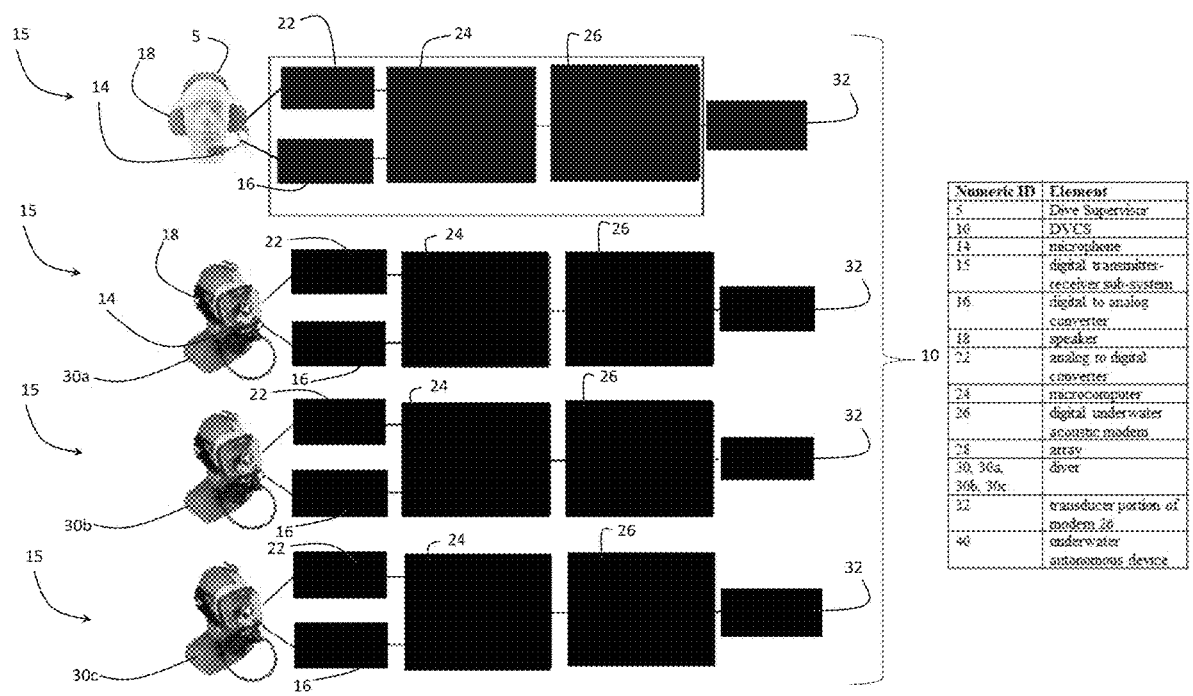
FIG. 4 is a representation of the connectivity of the system in FIG. 3.
Figure 5:
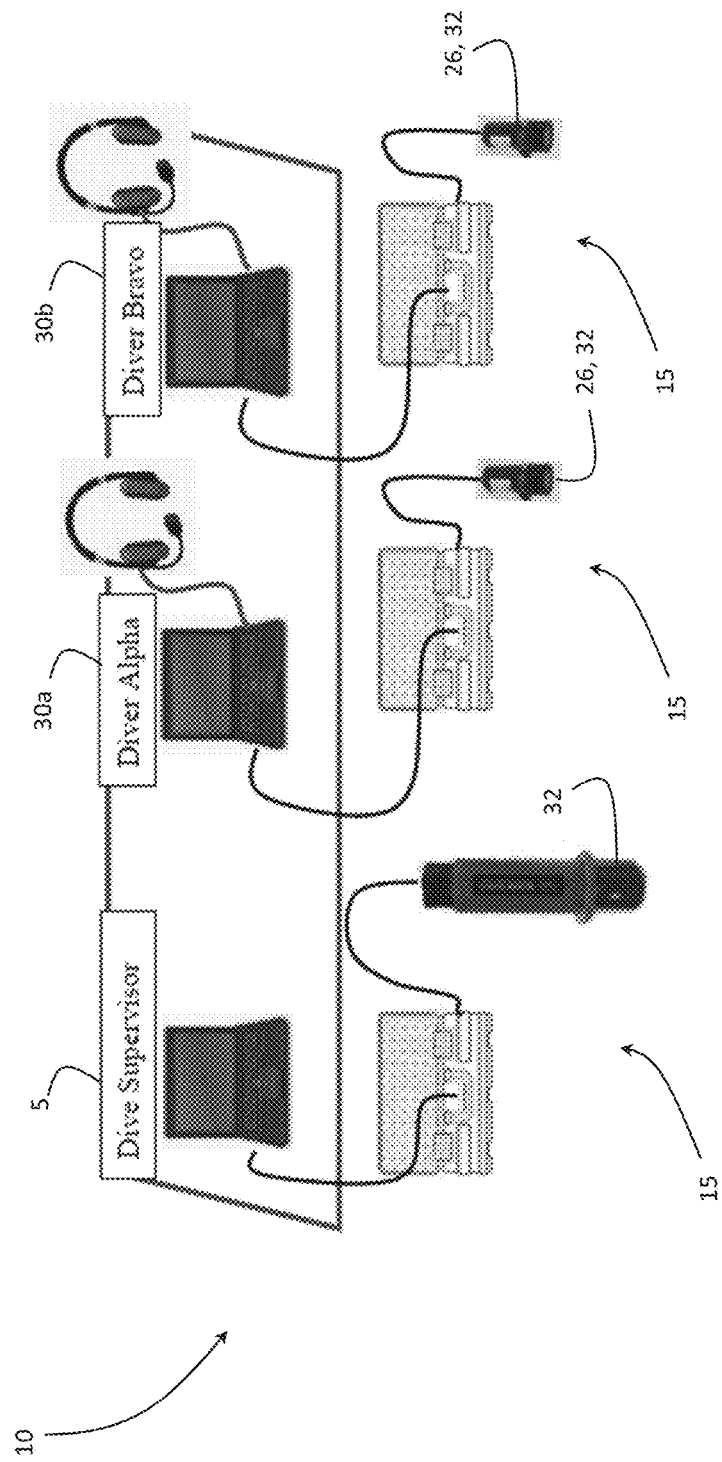
FIG. 5 provides a schematic of a prototype system of the diver's voice communication system.

Operation of DVCS 10 is demonstrated by the process flow diagram of FIG. 2. The system, as represented by FIGS. 2 and 4, enables transmission of a message from a first diver 30a to a second diver 30b or from a dive supervisor 5 or diver 30 to an AUV 40. In order to provide two-way communication, each diver 30*a* and diver 30*b* will have identical digital transmitter-receiver sub-systems 15. For simplicity, FIG. 2 merely depicts transmission of a message from diver 30*a* to diver 30*b*. Transmission of a signal from diver 30*b* to 30*a* will occur in an identical manner as described.

As indicated in FIG. 2, first diver 30*a* provides a verbal statement for communication to second diver 30*b*. First diver 30*a* activates digital transmitter-receiver sub-system 15 by a verbal command in a manner similar to activating the voice to text feature of a smart phone. Following activation, first diver 30*a* states the desired communication. The speech to text software programmed into microcomputer 24 converts the verbal statement of first diver 30*a* into a text message. The interface software programmed into microcomputer 24 parses the text input for Data and Range key words. One non-limiting example of Data key words includes: "Message". One non-limiting example of Range key words includes: "Range to <named diver>". Interface software identifies a key word and begins to collect the text message until a pause is detected. Subsequently, the interface software uses modem 26*a* associated with first diver 30*a* to send the text message to modem 26*b* associated with second diver 30*b*. Prior to sending the text message, microcomputer 24 uses the interface software to identify a Range key word, and sends a command using modem 26*a* requesting the range from modem 26*b* of second diver 30*b*. Remote modem 26*b* of second diver 30*b* sends the Range data to modem 26*a* of first diver 30*a* and central processor 24 associated with modem 26*a* uses the range data to determine distance to ranged diver 30*b*. Upon identification of the range to modem 26*b* associated with second diver 30*b*, microcomputer 24 associated with modem 26*a* used by first diver 30*a* directs the transmission of the text message to second diver 30*b*. Receiving array 28 through communication with GPS satellites may aid modems 26*a*, 26*b* in establishing the range from one modem 26*a* to the other modem 26*b*.

When modem 26*b* receives the text message, microcomputer 24 associated with modem 26*b* parses the received messages for text data and accesses text to speech software known as eSpeak (https://espeak.sourceforge.net/). The output of microcomputer 24 associated with modem 26*b* produces a verbal message corresponding to the text message as spoken by diver 30*a* which can be heard by diver 30*b* via an ear bud or other similar audio speaker 18.

Each microcomputer 24 associated with each modem 26 will be programmed to synchronize modems 26 with one another. A table of diver names or autonomous devices and modem identifiers, needs to be established before an underwater deployment. The table uses the following format: "Diver name/device"<space> modem identifier 0 to 249. Examples: "Soup 1; Mike 10; Steve 11; Robert 12;" see FIG. 7 for an example of an appropriate look up table. Upon input of the look up table into each digital transmitter-receiver sub-system 15, each diver 30 and dive supervisor 5, identified as Soup in FIG. 7's lookup table, will initiate synchronization of digital transmitter-receiver sub-system 15. Following synchronization, the resulting network of DVCS's 10 will be able to provide ranging, i.e. distance and positioning of divers 30 relative to one another and to each modem 26 used by a dive supervisor 5 located at the surface. Further, each modem 26 will be identified by a unique address thereby allowing other divers 30 to recognize the diver 30 sending the communication. Because each digital transmitter-receiver sub-system 15 can recognize and identify each digital transmitter-receiver sub-system 15 of the resulting DVCS 10 network, divers 30 and supervisors 5 have the previously discussed ability to selectively send communications.

The above described DVCS 10 was tested by sending messages from a dive supervisor 5 at a dock via computer connected to an underwater modem to a simulated diver in a boat also using a computer and connected underwater modem at ranges from 200 meters to 1200 meters. The test of DVCS 10 utilized headsets, personal computers and modem equipment to simulate the operation of digital transmitter-receiver sub-system 15. The test demonstration included an open water demonstration with three operators: a dive supervisor 5, a simulated diver 30 on the dock for monitoring, plus a simulated diver 30 on the boat. The digital transmitter-receiver sub-system 15 in the test used a PC, headset, and acoustic modem interface. The test demonstrated communications at various distances up to 1200 meter distances between the supervisor 5 on dock and the simulated diver 30 in the boat. The test data shows number of messages received at distances from 100 m to 1200 m. 102 total messages exchanged and received: 48 from diver 30 and 54 from Supervisor 5. The successful messages in this data set were received were by simulated diver 30 collocated at the dock with simulated dive supervisor 5. The following table provides the range over which messages were sent and the number of successful messages at each distance.

| Distances [meters] | total messages attempted | Successful messages |
|---|---|---|
| 100 m | 8 | 3 |
| 200 | 4 | 0 |
| 400 | 10 | 5 |
| 600 | 5 | 3 |
| 800 | 5 | 5 |
| 1000 | 10 | 9 |
| 1200 | 6 | 5 |

Other embodiments of the present invention will be apparent to one skilled in the art. As such, the foregoing description merely enables and describes the general uses and methods of the present invention. Accordingly, the following claims define the true scope of the present invention.

What is claimed is:

1. A diver communication system comprising:
at least one diver digital transmitter-receiver sub-system, including an underwater digital acoustic telemetry modem and a programmable device programmed with speech to text software and programmed with text to verbal message software;
a microphone;
an analog/digital converter;
a digital/analog converter;
a speaker;
an array of at least two remote receiving points, each remote receiving point in data communication with at least three global positioning satellites, each remote receiving point programmed to receive data from each diver digital transmitter-receiver sub-system and from the global positioning satellites and to track each diver digital transmitter-receiver sub-system relative to each other diver digital transmitter-receiver sub-system and the remote receiving points; and,
a dive supervisor digital transmitter-receiver sub-system comprising:

a headset with headphones and microphone for audio communications;

a visual display on a computer showing diver communications in text format and diver locations relative to the dive supervisor;

a second programmable device programmed with speech to text and text to verbal message software; and, an underwater digital acoustic telemetry modem;

wherein each diver digital transmitter-receiver sub-system and the dive supervisor digital transmitter-receiver sub-system are programmed to utilize data from the remote receiving points to provide distance values between each diver digital transmitter-receiver sub-system and between each diver digital transmitter-receiver sub-system and the dive supervisor digital transmitter-receiver sub-system.

2. The diver communication system of claim 1, wherein the diver digital transmitter-receiver sub-system speech to text software further includes artificial intelligence software programmed to adapt the speech to text software to compensate for voice distortions produced by a diver using a high pressure breathing gas mixture.

3. The diver communication system of claim 1, wherein each diver digital transmitter-receiver sub-system is programmed to utilize data from the remote receiving points to provide ranging and positioning between each diver digital transmitter-receiver sub-system.

4. The diver communication system of claim 1, wherein the programmable device includes a program, which can send commands, to an underwater autonomous device through the digital acoustical telemetry modem to control the underwater autonomous device.

5. The diver communication system of claim 1, wherein the diver digital transmitter-receiver sub-system includes a set of medical sensors suitable for monitoring at least one of: temperature, blood pressure, heart rate, echocardiogram, electroencephalogram, oxygen saturation (sO2), wherein the medical sensors are connected through analog-digital converters to an acoustic modem and data from the medical sensors is transmitted in parallel with voice communication.

6. The diver communication system of claim 5, wherein each acoustic modem includes a modem address which allows each diver digital transmitter-receiver sub-system to recognize the digital transmitter-receiver sub-system of a second diver digital transmitter-receiver sub-system and provides for communication between each diver digital transmitter-receiver sub-system and a command center thereby forming an underwater acoustic network.

7. The diver communication system of claim 1, wherein the diver digital transmitter-receiver sub-system includes external water sensors suitable for monitoring at least one of: water pressure (depth), water temperature, relative clarity, and wherein the external water sensors are connected through analog-digital converters to an acoustic modem and data from the external water sensors is transmitted in parallel with voice communication.

8. The diver communication system of claim 7, wherein each acoustic modem includes a modem address which allows each diver digital transmitter-receiver sub-system to recognize the digital transmitter-receiver sub-system of a second diver digital transmitter-receiver sub-system and provides for communication between each diver digital transmitter-receiver sub-system and a command center thereby forming an underwater acoustic network.

* * * * *